US006187810B1

(12) United States Patent
Kerek

(10) Patent No.: US 6,187,810 B1
(45) Date of Patent: *Feb. 13, 2001

(54) MACROCYCLIC COMPOUNDS MADE FROM SUBOXIDE UNITS

(75) Inventor: Franz Kerek, Munich (DE)

(73) Assignee: Donatur Dr. Kerek GmbH, Munich (DE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/101,401

(22) PCT Filed: Dec. 30, 1996

(86) PCT No.: PCT/EP96/05867

§ 371 Date: Apr. 15, 1999

§ 102(e) Date: Apr. 15, 1999

(87) PCT Pub. No.: WO97/25333

PCT Pub. Date: Jul. 17, 1997

(30) Foreign Application Priority Data

Jan. 5, 1996 (DE) ............................................. 196 00 301

(51) Int. Cl.$^7$ .................... A61K 31/352; C07C 15/56; C07D 493/22; C07D 311/02
(52) U.S. Cl. ........................ 514/453; 514/922; 514/950; 549/415; 585/19
(58) Field of Search ................................. 514/453, 922, 514/950; 549/275, 278, 381, 384, 415; 585/19

(56) References Cited

U.S. PATENT DOCUMENTS 2,565,115  8/1951  Bates et al. .
2,720,483  10/1955  Stiller et al. .

OTHER PUBLICATIONS

Scott et al., "Biogenetic–type Synthesis of Polyketides part VIII," Tetrhedron, vol. 27, No. 14, pp. 3025–3028, 1971.
Money et al., "Pyrone Studies–I," Tetrahedron, vol. 23, No. 8, pp. 3435–3448, 1967.
Barinaga, M., "Carbon Monoxide: Killer to Brain Messenger in One Step", Science, vol. 259, p. 309, Jan. 15, 1993.
Chapman, J.R., Practical Organic Mass Spectrometry, 2d ed., pp. 202–205, John Wiley & Sons, New York 1993.
Clemens, M.J., "Cytokines," The Medical Perspectives Series, pp. 102–111, Oxford 1991.

Collier, R.J., and Kaplan, D.A., "Immunotoxins," pp. 44–52, Heidelberg 1988.
Corry et al., "Primarily Vascularized Allografts of Hearts in Mice," Transplantation, vol. 16, No. 4, pp. 343–350, The Williams & Wilkins Co., 1973.
Di Bartolo et al., "Evidence for an Endogenous Ouabain–like Immunoreactive Factor in Human Newborn Plasma Coeluted with Ouabain on HPLC," Life Sciences, vol. 57, No. 15, pp. 1417–1425, Elsevier Inc. 1995.
Harris et al., "Development of an Immunoassay for Endogenous Digitalislike Factor," Hypertension, vol. 17, pp. 936–943, 1991.
Hoffman, B.F. and Bigger Jr., J.T., "Digitalis and Allied Cardiac Glycosides", The Pharmacological Basis of Therapeutics, 8th ed., pp. 814–839, Pergamon Press, New York 1991.
Huntress et al., "Carbon Suboxide in Comet Halley?," Nature, vol. 352, pp. 316–318, Jul. 25; 1991.
Jentsch et al., "Ubiquitin–conjugating Enzymes: Novel Regulators of Eukaryotic Cells," Trends in Biochemical Sciences, vol. 15., pp. 195–198, May 1990.
Kappe, T. and Ziegler, E., "Carbon Suboxide in Preparative Organic Chemsitry," Angewandte Chemie, vol. 13, No. 8, pp. 491–504, Aug. 1974.
Lehn, J.M., Supramolecular Chemistry: Concepts and Perspectives; A Personal Account, Chapter 2.3, pp. 17–18, VCH Weinheim 1995.
Schoner, W., "Endogenous Digitalis–like Factors," Progress in Drug Research, vol. 41, pp. 249–291, 1993.
Sercarz, E.E. and Datta, S.K., "Autoimmunity," Current Opinion in Immunology, vol. 6, pp. 875–881, 1994.
Smith et al., "The Structure and Properties of Carbon Suboxide Polymer," Inorganic Chemistry, vol. 2, No. 4, pp. 829–838, Aug. 1963.
Snyder, S.H. and Bredt, D.S., "Biological Roles of Nitric Oxide," Medicine, vol. 5, pp. 22–29, May 1992.
Verma et al., "Carbon Monoxide: A Putative Neural Meesenger," Science, vol. 259, pp. 381–384, Jan. 15, 1993.

Primary Examiner—Joseph K. McKane
Assistant Examiner—Taofiq A. Solola
(74) Attorney, Agent, or Firm—Sughrue, Mion, Zinn, Macpeak & Seas, PLLC

(57) ABSTRACT

The invention relates to macrocyclic substances which are bioregulatory active and a method for their synthetic production as well as its isolation from various starting materials. The application of these active substances as such or in combination with other active substances for enzyme regulation and bioregulation is also described.

24 Claims, 7 Drawing Sheets ns APPLN. is a 371 of PCT/EP96/05867 filed Dec. 30, 1996.

MACROCYCLIC COMPOUNDS MADE FROM SUBOXIDE UNITS

FIELD OF THE INVENTION

The invention relates to macrocyclic substances which are bioregulatory active and a method for their synthetic production as well as its isolation from various starting materials. The application of these active substances as such or in combination with other active substances for enzyme regulation and bioregulation is also described.

BACKGROUND OF THE INVENTION

The proper course of biochemical processes and the optimal function of biological immune mechanisms is ensured by numerous bioregulatory active substances (Rompp Lexikon page 3826 "Regulation"). From a chemical standpoint, bioregulatory active substances known up to now are peptides, carbohydrates, steroids or lipids, whereby these structural elements can also occur together (for example, glycopeptides, lipoproteins). Furthermore, the application of bioregulatory active substances for the therapy of diseases which are caused by disturbed functions of one or more of these regulation mechanisms is known. The therapeutic use of steroid hormones, corticosteroids and cardiac glycosides as well as growth hormones or blood coagulation factors are some of the many examples in this sense. However, pharmacotherapy with substances of this type is very often accompanied by damaging side-effects, and therewith, considerably limited. A detailed consideration of these aspects is to be found in Goodman and Gilman's "The Pharmacological Basis of Therapeutics", 8th Ed., New York, 1991. For example, with cardiac glycosides, the positive inotropic, therapeutically useful action is compromised by a cardiotoxic side-effect, and consequently, therapeutic doses must be very rigorously limited. As a further example, the application of corticosteroids may be mentioned where the therapeutic use is only recommended in very severe cases and only for a limited time due to a series of very severe side-effects such as myopathy, osteoporosis, psychic disturbances, increased infection susceptibility, etc.

Despite considerable efforts to treat immunologically caused disease syndromes with immunoregulatory active substances, previous clinical tests are not convincing. The purpose of such immunotherapeutic applications would be to accomplish the basic therapy for autoimmune diseases such as rheumatoid arthritis and multiple sclerosis, among others, which has not been found to date. According to E. Sercarz and S. K. Datta "Autoimmunity" in Current Biology 6, 875–881 (1995), these autoimmune diseases have mostly been caused by disturbed immunoregulation. For fighting severe disease syndromes which are characterized by a considerably weakened immune system, such as carcinosis or AIDS, the previous therapeutical uses of immunoregulatory substances has yielded little.

Several bioregulatory peptides and proteins have been characterized as reported in the Monograph from M. J. Clemens "Cytokines", Oxford 1991. That cytokines play an important role in different carcinoses, in autoimmune diseases and in viral infections (including AIDS) has also already been reported several times. Despite this, wider therapeutic applications of these and other bioregulatory proteins and peptides are still lacking to a large extent. One of the causes for this certainly lies in the often very laborious production technologies: the extractions and subsequent purifications of bioregulatory active substances from human or animal tissue fluids, where they are present in only very small amounts, is completely unsuitable for providing therapeutically needed amounts. The danger of allergic side-effects and/or anaphylactic reactions which, despite their rare occurrence, represent a considerable risk factor for human therapy that still exists with gene technologically produced bioregulatory polypeptides or glycoproteins. The fundamental problem of the therapeutic applications of several "in vitro" highly active polypeptide factors lies in the fact that they demonstrate "in vivo" entirely different, mostly very much weaker activity. On the one hand, numerous physical and enzymatic barriers impede the externally administered peptides and proteins from reaching the location of the pathological event (focus of inflammation, cancerous ulcer, etc.). On the other hand, they are quickly neutralized and metabolized by the endogenous enzymes and other factors present there. With peroral administration of active substances of a peptide, glycopeptide and glycosidic nature, these substances are already rendered practically ineffective in the gastrointestinal system by several degradation processes.

However, a relatively fast degradation of bioregulatory active substances of peptidic or glycopeptidic nature must also be taken into account with a delivery "per os". In order to entirely target the therapeutically effective concentration to the location of the pathological event or manifestations, such as at the focus of inflammation or at the cancerous ulcer, a masked delivery of the active substance has been performed for example. Something similar was described by R. Collier and D. Kaplan in "Immuntoxine", Heidelberg 1988, in connection with the use of toxins which could be purposefully employed bound to monoclonal antibodies (drug targeting). However, the treatment technique is still very complicated and only remains restrictively applicable for specific cases. For regulatory active substances, the bioavailability is not only dependent on stability, but also on purely physical processes, such as solubility and membrane permeability. This concerns making the water solubility of lipophilic substances possible in plasma or making the membrane permeability of hydrophilic active ingredients such as $Na^+$ or $K^+$ ions possible. For example, the mitochondria membrane is normally not permeable to potassium ions. Macrocyclic antibiotics such as nonactin or valinomycin make this permeability possible through the organic envelopment of the corresponding ions.

Since 1967, the year of discovery of the "crown ethers", numerous new compounds have been produced which have a macroring structure and make a crown or cryptate-like covering of inorganic ions or smaller molecules possible. However, important prerequisites for a direct therapeutic application of such cryptate-forming macrocyclic substances are a low toxicity and good bioassimilation, which is only seldom fulfilled by the synthetically produced cryptand reagents.

Many fundamental bioregulatory mechanisms are controlled by the so-called sodium pump. This enzyme has the ability to pump sodium ions from the insides of cells to the outside and simultaneously transport potassium ions in the opposite direction. The energy consumption is delivered by a coupled hydrolysis of adenosine triphosphate (ATP). This pump is identical with the enzyme referred to as the $Na^+$, $K^+$-ATPase and is ubiquitously distributed. Several important cellular functions are controlled by this $Na^+$,$K^+$-ATPase such as cell volume, heat production, intracellular free $Ca^{2+}$ ion concentration, neuronal transmission, muscle contraction or membrane potential.

In numerous immunoregulatory processes, important phases are also controlled by the $Na^+$,$K^+$-ATPase, and thus, the sodium pump also acquires a fundamental roll in immunoregulation. Despite this general distribution and significance, the regulation mechanism of this enzyme has not yet been clarified. The so-called "cardiac glycoside receptor site" of the enzyme is suspected as the functional location for the bioregulation of the sodium pump. The cardiac glycosides present in several plant species are bound to this site with high affinity and exert their cardiotonic, but also their cardiotoxic effect. However, their toxicity proves that they are not identical with the endogenous ligands of this enzyme. In the paper "Endogenous digitalis-like factors" by W. Schoner in Progress in Drug Research, 41, 249–291 (1993), it is reported that the chemical nature and the structure of these endogenous bioregulatory substances could not yet be established despite a large research effort. Up to now, no sufficient amount of these endogenous factors could be isolated from animal tissue and fluids in order to make an exact characterization and structure determination possible. The activity of the $Na^+,K^+$-ATPase, and therewith several bioregulatory mechanisms, could be effectively controlled with factors which are identical or structurally similar to these endogenous ligands.

Recently, several simple inorganic substances have been found which participate in bioregulatory processes. However, it is important to note that all of these inorganic substances are only used as simple messenger substances or effectors. They fundamentally lack the three-dimensional structure necessary for exerting a bioregulatory action and the capability for structure specific action coupled therewith. In the paper "Biological Roles of Nitric Oxide" by S. Snyder and D. Bredt in Scientific American, 1992 (5) 22–29, it is reported that this gaseous compound is a functional effector in the control of the non-specific immune response. In the organism, nitric oxide had a very short life time in order to exert its local, mostly toxic effect and is always produced "in situ". When the phagocytes of the immune system, the so-called macrophages, are activated with bacterial toxins or cytokines, they can produce relatively large amounts of nitric oxide within hours and this is employed as an immunological weapon. It is assumed that further simple gaseous compounds also participate in bioregulatory processes. Ethylene, for example, is known as an important factor in plant biology. Carbon monoxide participates in the physiological regulation of the cyclization of guanosine monophosphate (GMP) as was reported by A. Verma in Science, 259, 381 (1993).

Only very little has been reported up to now on the biological action of another carbon oxide, the much more seldom found $C_3O_2$. It is only known that this concerns a compound which is gaseous at room temperature (bp 7° C.), is irritating to mucus membranes and smells of mustard oil and acrolein. Carbon suboxide represents a relatively strong blood toxin which irreversibly binds hemoglobin; the tolerability limit in mice lies at 0.2–0.4% $C_3O_2$ in dry air. $C_3O_2$ reacts with water and forms malonic acid. However, without traces of mineral acids, this reaction does not proceed so fast as it was previously claimed. It is suspected that, aside from carbon monoxide, the primitive reducing earth atmosphere also contained considerable amounts of $C_3O_2$, and recently, evidence of its possible presence in interstellar space was found as reported by W. Huntress et al. in Nature, 352, 316–318 (1991). However, until now there is no concrete evidence for the possible presence of $C_3O_2$ in biological fluids. Considering the water sensitivity of the monomer gas as well as the amorphous polymer, a possible biological role has been mostly excluded a priori. The hypothesis of H. Yanagawa and F. Egami in Precambrian Research, 14, 75 (1981), whereby the water reactive amorphous polymer could have been a possible starting material for the original synthesis of simple organic compounds, has been considered as fundamentally possible. Gaseous $C_3O_2$ more or less quickly forms amorphous polymers which are yellow to intensive red-brown colored. Only very little concrete knowledge is known on the structure of these polymers. In general, they are described as a non-homogeneous amorphous mass which was also earlier designated as "red carbon". The chemical properties of carbon suboxide and its polymers are reviewed in the paper by T. Kappe and E. Ziegler, Agnew. Chem., 86, 529 (1974). The polymerization products are partially soluble in water or in diluted alkalines, whereby intensive yellow to dark brown colored solutions are formed. Several hypothetical formulae have been proposed for the structure of these amorphous, irregular polymers, but none of them could also be experimentally confirmed. As the most probable, a graphite-like, hexagonal lattice structure is suspected which is unsaturated at the periphery and must be correspondingly unstable. This hypothesis was described in detail in the paper by N. S. Smith and D. A. Young in Inorganic Chemistry 2, 829 (1963).

It is further known that several biologically highly effective substances in plasma are not found as such, but rather as conjugates. For example, steroid hormones are present in blood plasma as their sulfate or glucuronate conjugates and their degradation products are also eliminated as such conjugates. Not infrequently, these conjugated steroids demonstrate even better therapeutic properties in comparison with the pure active substance, as was described for conjugated estrogen steroids according to U.S. Pat. No. 2,565,115 and U.S. Pat. No. 2,720,483 or for dehydroepiandrosterone sulfate (DHEAS). The above mentioned conjugations regulate the biological availability and the assimilation of these steroid active substances and can therewith explain the improved therapeutic properties. Relatively little is known about the regulation of the bioavailability of polypeptidic active substances by the formation of corresponding conjugates. The enzymatic conjugation of proteins with ubiquitin also has regulatory functions as was described in Trends Biochemical Sciences 15, 195 (1990). The suitable conjugation of polypeptidic substances could attain a breakthrough in the therapeutic applications of these active substances. As a known example, the search for retard acting insulin is to be mentioned. It is known that the therapeutic functional time of insulin is considerably prolonged by addition of zinc salts or of protamine sulfate. However, these additives can cause different side-effects. A suitable conjugate which should ensure a retarded release of insulin has been tried by numerous inventors, but until now has not be realized.

DESCRIPTION OF THE INVENTION

FIELD OF THE INVENTION

Object of the present invention is to provide new macrocyclic substances with bioregulatory activity in which the above mentioned disadvantages do not appear and which bring about the recovery of the disturbed bioregulatory mechanisms in diseases. Additionally, the active substances should clearly improve the therapeutic effect and the bioavailability of known medicaments.

This object is solved according to the invention by the 39 features of claims 1 to 39.

STRUCTURE DESCRIPTION

The substances according to the invention are chemical compounds whose structural frame is built from the simple inorganic carbon suboxide $C_3O_2$ by cyclooligomerization. Although carbon suboxide O=C=C=C=O itself and the amorphous polymers formed from it are known as reactive, water sensitive substances, the inventor could astonishingly obtain particular water stable cyclooligomeric carbon suboxide structures. The basic prerequisite for their water-stability is that these structures no longer contain the reactive cumulated C=C and C=O double bonds of carbon suboxide. This is solved according to the invention such that several, preferably 4, 6, 8 or 10, carbon suboxide molecules are cyclomerized to condensed 4-pyrone or 2-pyrone rings and these structures are additionally closed in double-strained macrorings Cyclohexameric Carbon Suboxide com-$(C_3O_2)_6$ The molar mass M=408.19 determined experimentally by mass spectrometry corresponds to the formula $C_{18}O_{12}$ and at the same time to the six-fold molar mass of the carbon suboxide M=68.032. For the structure, several isomer possibilities are conceivable, for example with condensed 2-pyrone rings or with head-to-head condensed 4-pyrone rings, or the following depicted structure with six alternating head-to-tail condensed 4-pyrone rings which is assumed as the most probable based on spectral and other properties.

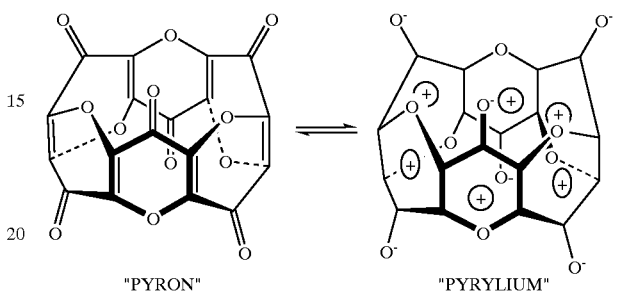

"PYRON"  "PYRYLIUM"

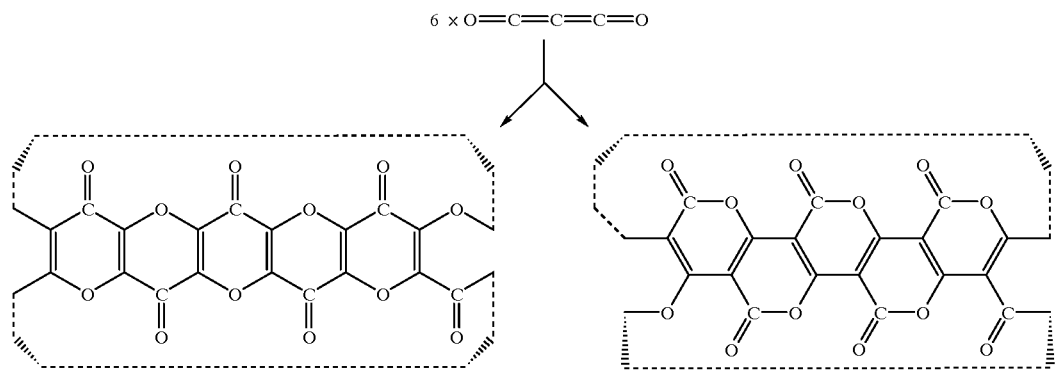

Basically, these frames which are built from cyclooligomeric carbon suboxide are not organic compounds and can be considered to belong, as well as carbon suboxide itself, to inorganic chemistry.

The chemical formula of the cyclooligomeric carbon suboxide frames closed to macrorings is as follows:

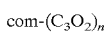
com-$(C_3O_2)_n$ wherein n denotes the degree of cyclooligomerization of $C_3O_2$ and com symbolizes the above specified cylco oligomeric and macroring type of linkage of these units.

Furthermore, the inventor has found that among the endlessly large number of principally possible structures of cyclooligomeric carbon suboxides closed in macrorings, only a few with certain n values are particularly stable. Those cyclooligomeric macrocyclic frames are preferred in which the number n equals 4, 6 or 10 or is a multiple of 4, 6 or 10 in the formula

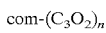
com-$(C_3O_2)_n$

Active substances according to the invention with larger preferred n values can also be considered as multiples of the smaller cyclooligomeric carbon suboxide units with the formula com-$(C_3O_2)_n$. The first member of such series of cyclooligomeric and macroring closed carbon suboxides defined here has a particular importance as described in detail for the:

The actual electron distribution lies presumably between the here depicted limit structures denoted as PYRON and PYRILIUM but can take solvent and medium dependent other, more or less polarized tautomeric electronic structures.

Hydroxy-pyran and Pyrylium Salt Derivatives

Figure 1:
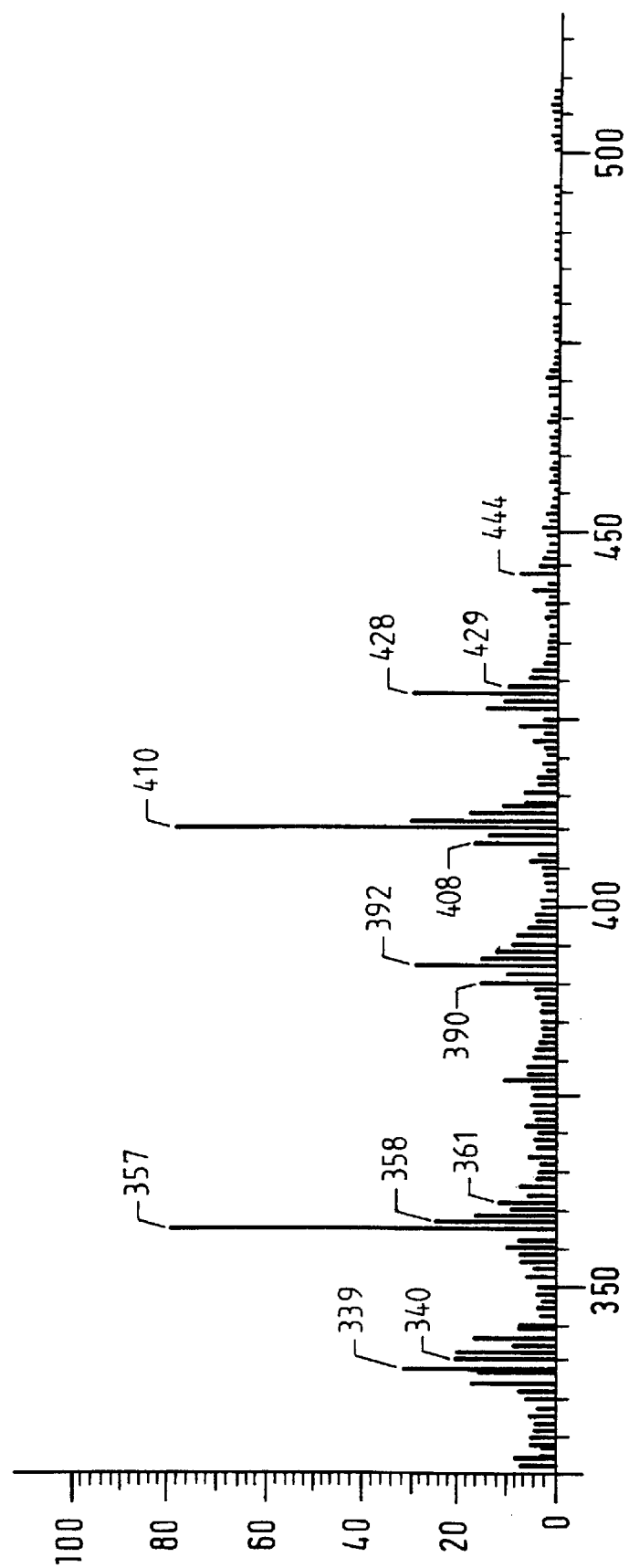
FIG. 1: Electroionization mass spectrum of the com-$(C_3O_2)_6$ in water.

The existence of some reduced derivatives of the cyclohexameric carbon suboxide with the general formula $(C_3O_2)_6 \cdot H_{1-6}$ is also visible in the mass spectrum (FIG. 1). In aqueous solution, the active substances according to the invention can also be present as hydroxy-pyran derivatives. The general formula of the reduced hydroxy-pyran derivatives formed by several-fold addition of hydrogen is:

com-$(C_3O_2)_n \cdot H_m$ wherein the number m of the bound hydrogen atoms is limited by the number n of the exacyclic oxygen atoms, and thus, m is $\leq n$.

The fully reduced hydroxy-pyran derivative has in the case of the cyclohexamer the formula

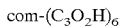
com-$(C_3O_2H)_6$ and the molar mass M=414.24 and presents a particular importance for the formation of inorganic and organic derivatives and is, together with com-$(C_3O_2)_6$, the basic unit in the cyclohexameric series for the formation of self-associates and different derivatives. The presumed 4-hydroxy-pyran structure of the cyclohexameric carbon suboxide com-$(C_3O_2H)_6$ is depicted as follows:

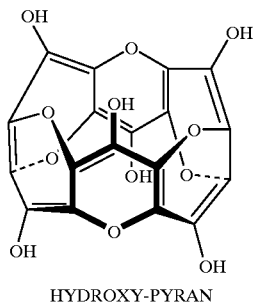

HYDROXY-PYRAN

In general, in the presence of strong ionic agents like acids or bases as well as several easily dissociating salts, the formation of pyrylium salt compounds with anions An and cations Ka are considered. The chemical formula of the pyrylium salt derivatives which are formed from the active substances according to the invention with an acid, a base or a salt compound of the general formula Ka.An is:

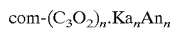

com-$(C_3O_2)_n$·$Ka_n An_n$ wherein Ka and An are the cationic the anionic counter ions which neutralize the altogether 2n zwitterionic charges of the pyrylium frame. The structure of the pyrylium salt compounds can be depicted as follows, wherein the counter ions are not exactly localized in the aqueous solution.

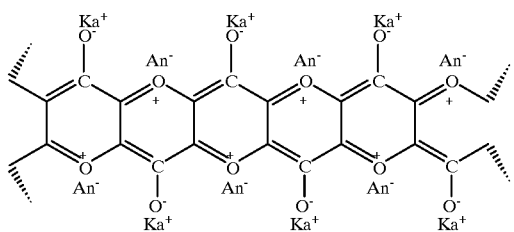

The anionic An and cationic Ka counter ions can be present

- as individual and uniform inorganic or organic cations and anions, for example all Ka=$Na^+$ and all An=$Cl^-$,
- as a mixture of inorganic or of organic cations and anions, for example in a relationship corresponding to the physiological concentrations of these ions or
- as zwitterionic compounds themselves containing both counter ions such as amino acids, betaine, ionic soaps.

In water, the pyrylium salt derivatives of the active substances according to the invention are mostly very soluble. The somewhat lower solubility of pyrylium salts with anions such as chloride of sulfate in acetone or ethanol is used in the isolation according to the invention of the active substances described here. In physiological fluids, the zwitterionic charges of the active substances are neutralized by the anions and cations present there. Accordingly, it is more appropriate to speak of a statistic distribution of the counter ions than of chemically unified salt compounds of a certain ion.

Certain complexes formed with metal ions, preferably transition metal ions such as Fe(III), Sb(III), Cd(II), Pt(II), Au(III), Pb(IV), can be used for the isolation and for the detection of the active substances according to the invention. The compounds formed with complex inorganic or organic anions such as $SCN^-$, $BF_4^-$, $Cr_2O_7^{2-}$, $MnO_4^-$, picrate, reineckate, can also be used for isolation and for detection.

Adducts, Conjugates

The formation of molecular adducts with inorganic elements or with organic compounds is promoted by the strong capacity for association of the cyclooligomeric and macroring closed carbon suboxides according to the invention. The stochiometric or non-stochiometric adducts with organic compounds are denoted as conjugates. Cyclooligomeric and macroring closed carbon suboxide can form stable adducts with several—in the case of cyclohexamers with preferably 2 to 6—molecules of ammonia, organic amines, amino acids, peptides or other substances with amine function. Natural amino acids, biological amines and their derivatives with amine function are particularly comprised within the scope of this invention. The general formula of these amine adducts is:

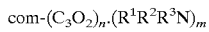

com-$(C_3O_2)_n$·$(R^1R^2R^3N)_m$ wherein $R^1$, $R^2$ and $R^3$ is each a hydrogen atom or an organic residue and m is a number from 1 to n, n having the meaning as previously defined.

Figure 2:
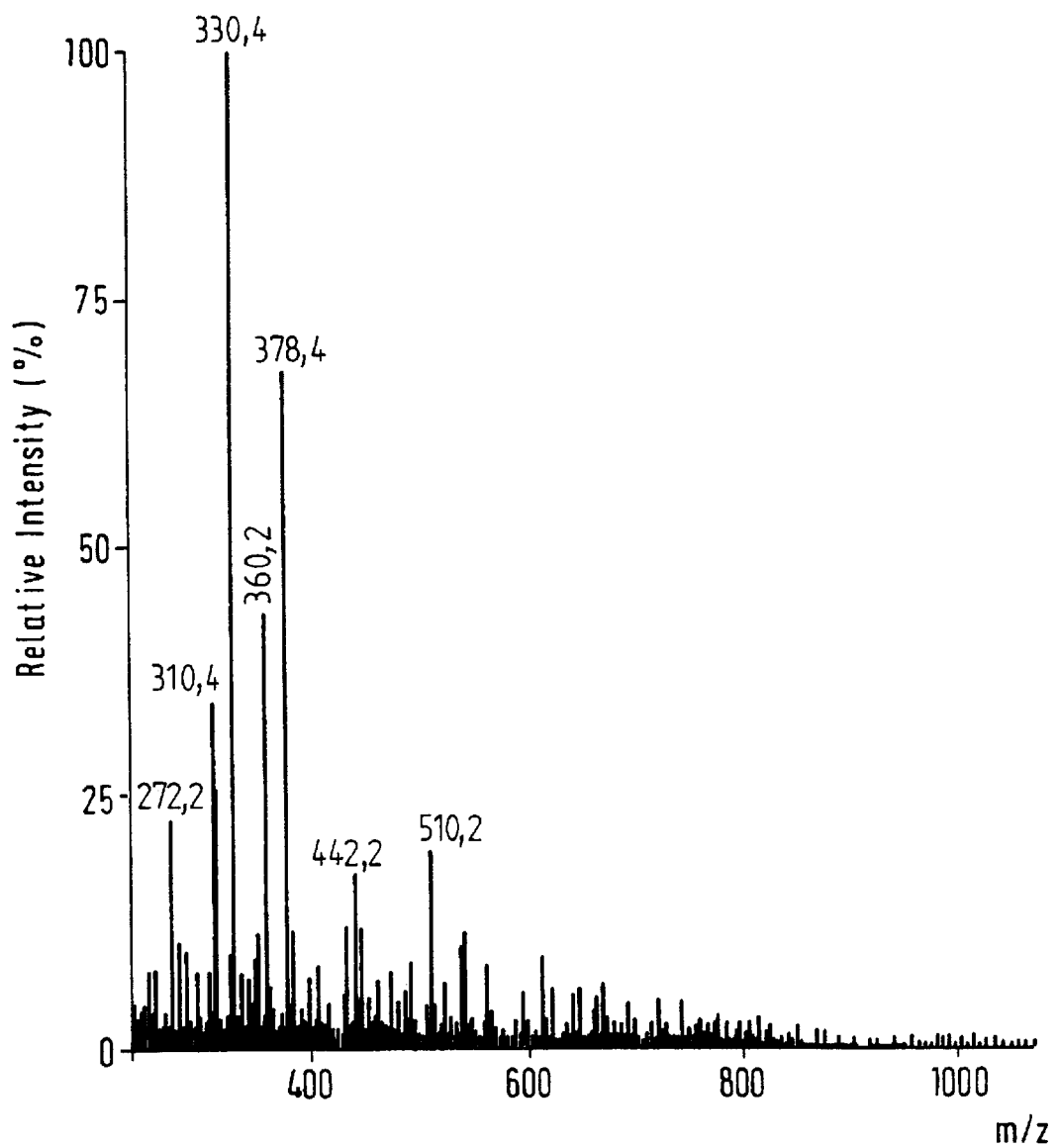
FIG. 2: Electrospray mass spectrum of the amine complexes com-$(C_3O_2)_6.(NH_3)_2$ and com-$(C_3O_2)_6.(NH_3)_6$.

Experimentally, the molar mass of the diamine adduct of the cyclohexamers with the formula com-$(C_3O_2)_6$·$(NH_3)_2$ was established by ES mass spectrometry as M=442.2 and the hexamine adduct with the formula com-$(C_3O_2)_6$·$(NH_3)_6$ as M=510.4 (FIG. 2). With the diamine adducts, the two ammonia or amine molecules are probably bound to the carbonyl groups of the pyrone rings by hydrogen bonds. Since in the case of the hexamine complexes the internal cavity of the macroring structure is already involved, these are also considered as host-guest complexes.

Host-Guest Complexes

The second particularly important structural property of the active substances according to the invention is accomplished in such a manner that the condensed pyrone or hydroxypyran rings additionally form macrorings according to the invention, preferably in cylindrical form. The molecular dimensions of this ring structure are suitable for the inventive formation of host-guest complexes according to the invention. As "guests", elements smaller molecules or molecule fragments are considered which fit sterically into the cylindrical cavity, and/or are bound to their periphery by specific binding forces. The form and dimensions of the cylindrical macroring structure of the cyclohexameric carbon suboxide are taken from the following figure.

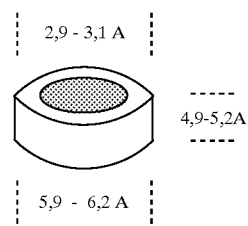

Cations such as potassium, ammonium, silver or rubidium or anions such as fluoride, chloride, formate or rhodanate fit well in the inner cylindrical cavity of the macroring of the cyclohexamers with an inner diameter of 2.9 to 3.2 Å and a height of 4.9 to 5.2 Å. In the applications according to the invention, an ion or a neutral element or molecule is present in the cavity of the cylindrical macroring structure of a com-$(C_3O_2)_6$ unit and is enveloped by this. The molar mass measured by mass spectrometry corresponds to the sum of the individual components and proves that these host-guest complexes are independent compounds. The inventor has experimentally established the existence of host-guest complexes of the cyclohexameric carbon suboxide with smaller inorganic or organic compounds, generally denoted with Y, such as ammonia, hydroxylamine, methanol, ethanol, propanol, acetone, dichloromethane, chloroform, acetylcholine, formic acid, acetic acid as well as with several amino acids and carbohydrates. According to the invention, the substance Y or a part of its structure is present as a "guest" in the inner cavity of the active substance according to the invention as it is to be taken from the following figure.

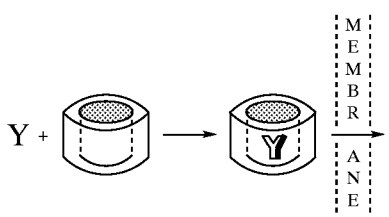

Through this "envelopment" certain properties of the substance Y are "masked" and the newly obtained properties according to the invention, such as improved membrane transport and bioavailability, are made possible.

Active Substances of Different Molar Mass $M \leq 2,000$ Dalton

The above described cyclooligomeric carbon suboxides with the formula, com-$(C_3O_2)_n$, wherein n is 4, 6, 10, 12 or 18, as such or in hydroxy-pyran form with the formula com-$(C_3O_2H)_n$, and all their derivatives, adducts, host-guest complexes whose molar mass lies below this limit belong to this low molar mass category. The self-associates formed from 2 to 4 cyclohexameric units are also considered as low molar mass active substances. The existence of the com-$(C_3O_2)_{12}$ with the molar mass M=816 D and of the com-$(C_3O_2)_{18}$ with M=1,224 D identified by the inventor can also be explained therewith.

M>2,000

At first, the active substances classified here appear as a mixture of compounds with heterogeneous molar mass. However, a closer analysis has proven that, despite the principally endlessly large number of possible compounds, only very few, i.e. those with a particular molecular size, are obtainable and capable of being identified.

Figure 3:
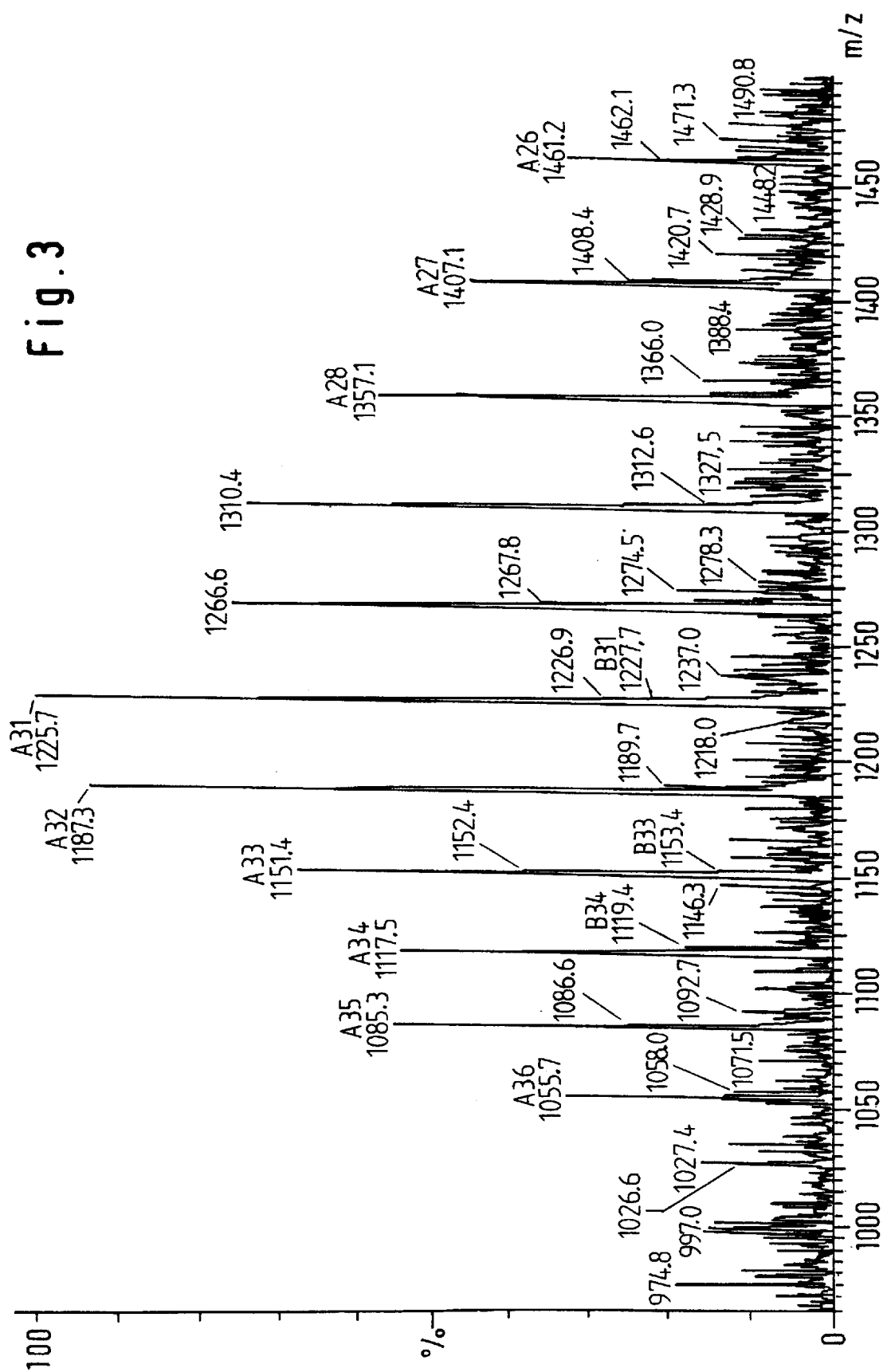
FIG. 3: LC-coupled electrospray mass spectrum of the multi-charged units of com-$(C_3O_2)_n$ with n=558.

The LC-MS, Electrospray mass spectrum (FIG. 3) of an active substance in water-acetonitrile solution demonstrates that a series of multiply charged ions (m/z) is present. The measured m/z=1,225.7 Dal of the most intensive component A31 corresponds exactly to the protonated molecule of the formula com-$(C_3O_2)_{18}$. The experimental molar mass of the corresponding polymer is determined with the aid of the formula M=n [m/z-1] (page 202, Practical Mass Spectrometry by J. R. Chapmann, J. Wiley, New York, 1993) as M=31×1,224.6=37,962.6 Dal.

The molar masses of some of the identified compounds are to be taken from the following table.

| molar mass found | | | calculated molar mass /D/ | |
| --- | --- | --- | --- | --- |
| HP-GP, PAGE* | MS** | n | com-$(C_3O_2)_n$ | com-$(C_3O_2H)_n$ |
|  | 408.2 | 6 | 408.2 |  |
|  | 414.2 | 6 |  | 414.2 |
|  | 680.6 | 10 | 680.3 |  |
|  | 816.4 | 12 | 816.4 |  |
|  | 1,224.6 | 18 | 1,224.6 |  |
| ≈2,500 |  | 36 | 2,449.2 |  |
| ≈4,100 | 4,084.2 | 60 | 4,082.0 |  |
| ≈4,100 | 4,134.0 | 60 |  | 4,142.5 |
| ≈5,000 | 4,900.8 | 72 | 4,898.4 |  |
| ≈5,000 | 4,976.6 | 72 |  | 4,970.9 |
| ≈10,000 | 10,065.2 | 144 |  | 9,941.9 |
| ≈12,500 | 12,656.8 | 186 | 12,654.2 |  |
| ≈15,000 |  | 216 | 14,912.0 |  |
| ≈30,000 |  | 432 |  | 29,825.7 |
| ≈38,000 | 37,963.3 | 558 | 37,962.6 |  |
| ≈60,000 |  | 864 |  | 59,651.4 |
| ≈120,000 |  | 1,728 |  | 119,302.7 |

Figure 4:
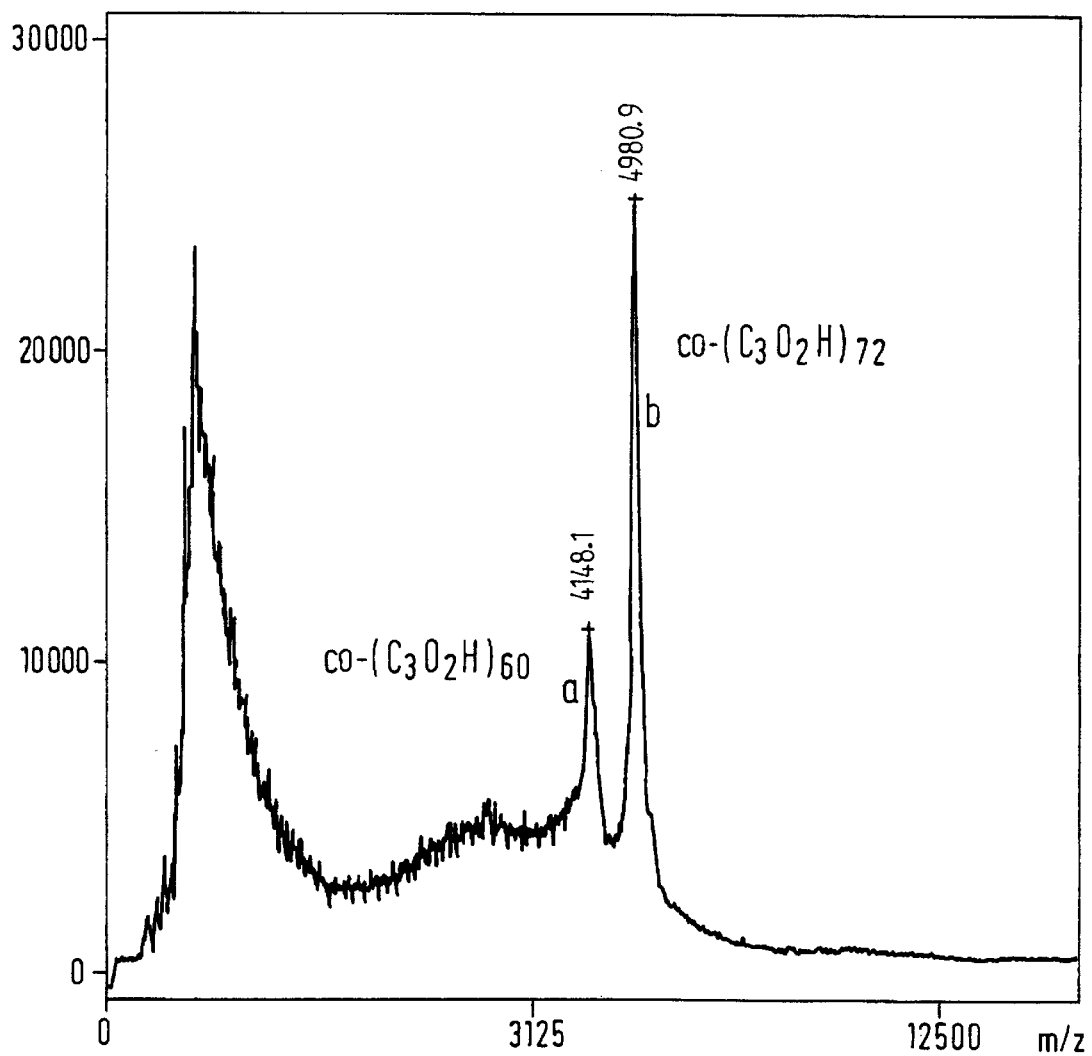
FIG. 4: MALDI-mass spectrum of the com-$(C_3O_2H)_{60}$ and com-$(C_3O_2H)_{72}$.

*in comparison with known standards
**by MALDI the average value of three experimental measurements The measurements were carried out with the aid of MALDI mass spectrometry (MS), gel permeation chromatography (GP) or polyacrylamide gel electrophoresis (PAGE). As evident from the MALDI mass spectrum (FIG. 4), the corresponding compounds for n=60, and especially where n=72, are present is clearly larger concentrations than all others. The molar masses determined by this method correspond with very good accuracy to n=60 and n=72 in the formula com-$(C_3O_2H)_n$ of the hydroxy-pyran oligomers. These compounds can be considered either as cyclooligomers with n=60 or n=72 or as s=10- or s=12-fold self-associates of the cyclohexameric basic unit $\{$com-$(C_3O_2H)_6\}_s$. The physico-chemical and spectroscopic properties of these compounds com-$(C_3O_2H)_{60}$ and com-$(C_3O_2H)_{72}$ indicate a high structural symmetry which would be explainable for example with a spherical arrangement of 10, 12 or more com-$(C_3O_2H)_6$ units. A sandwich arrangement with pentagonal or hexagonal symmetry could also explain the neutralization of a large number of zwitterionic charges.

The experiments with the aid of polyacrylamide gel electrophoresis (PAGE) have shown a strong band in the region of M≈5 kD and optionally further lines at the molar mass values of ca. 10 kD, 12.5 kD, 15 kD, 30 kD, 60 kD and 120 kD. These correspond with acceptable accuracy to the degrees of oligomerization n=72, 144, 180, 216, 432, 864 and 1,728. Strangely enough, these numbers represent particular multiples of the numbers 6 and 12. With a 16.5% polyacrylamide concentration of the gel, the strongest band by far is present in the range M≈5 kD. However, if the same sample is applied to a different gel, for example with lower polyacrylamide content, the main band can appear at a two-fold greater region (≈10 kD). This anomaly is explained by specific association-dissociation equilibria of the active substances.

Association Equilibria and Membrane Transport

The inventor has also determined particular anomalies in the dialysis and ultrafiltration of the compounds with higher molecular weight. After a certain dialysis time, the larger, normally non-membrane permeable active substances were detectable on both sides of the membrane. The explanation for this is that the higher associates according to the following equation 1 dissociate into smaller membrane permeable forms and these reconstitute the larger self-associates in the outward dialysate. After longer dialysis time, an equilibrium develops on both sides of the membrane.

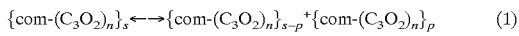

$$\{com\text{-}(C_3O_2)_n\}_s \leftrightarrow \{com\text{-}(C_3O_2)_n\}_{s-p} + \{com\text{-}(C_3O_2)_n\}_p \qquad (1)$$

wherein s=2, 3, 4, 5, 6, 10 or 12 as well as a multiple of these numbers and p<s. The equilibrium between a simple cyclooligomer and its multiply associated derivatives with a higher molar mass is dependent on numerous factors or can be influenced for example by the nature of the solvent, the pH value, the concentration of the alkali metal and other ions, the temperature and the conjugation with other substances present in the solution. The equilibrium (1) enables penetration of active substances according to the invention with larger molar mass into the intracellular space which are normally blocked to this access. In the external membrane space, the active substances according to the invention can be present as larger com-$(C_3O_2)_n$ compounds. Through dissociation according to equation (1), these active substances can pass through the membrane and thus arrive in the internal membrane space where they re-form the larger compounds by association.

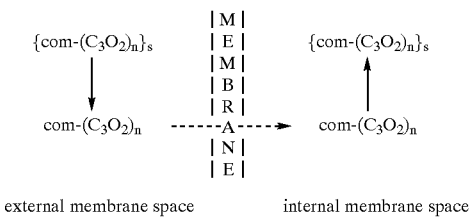

external membrane space    internal membrane space

Due to their stability, the larger self-associates can also serve for the physiological storage and the transport of active substances and thus reach the location of the pathological manifestation. They display their bioregulatory, therapeutic effect there as such or conjugated with other active substances. A "masked" membrane transport of a membrane impermeable substance Y can be carried out according to the invention in such a manner that this substance is "hidden" in the cylindrical inner cavity of the active substance.

Spectroscopic Characterization

Figure 5:
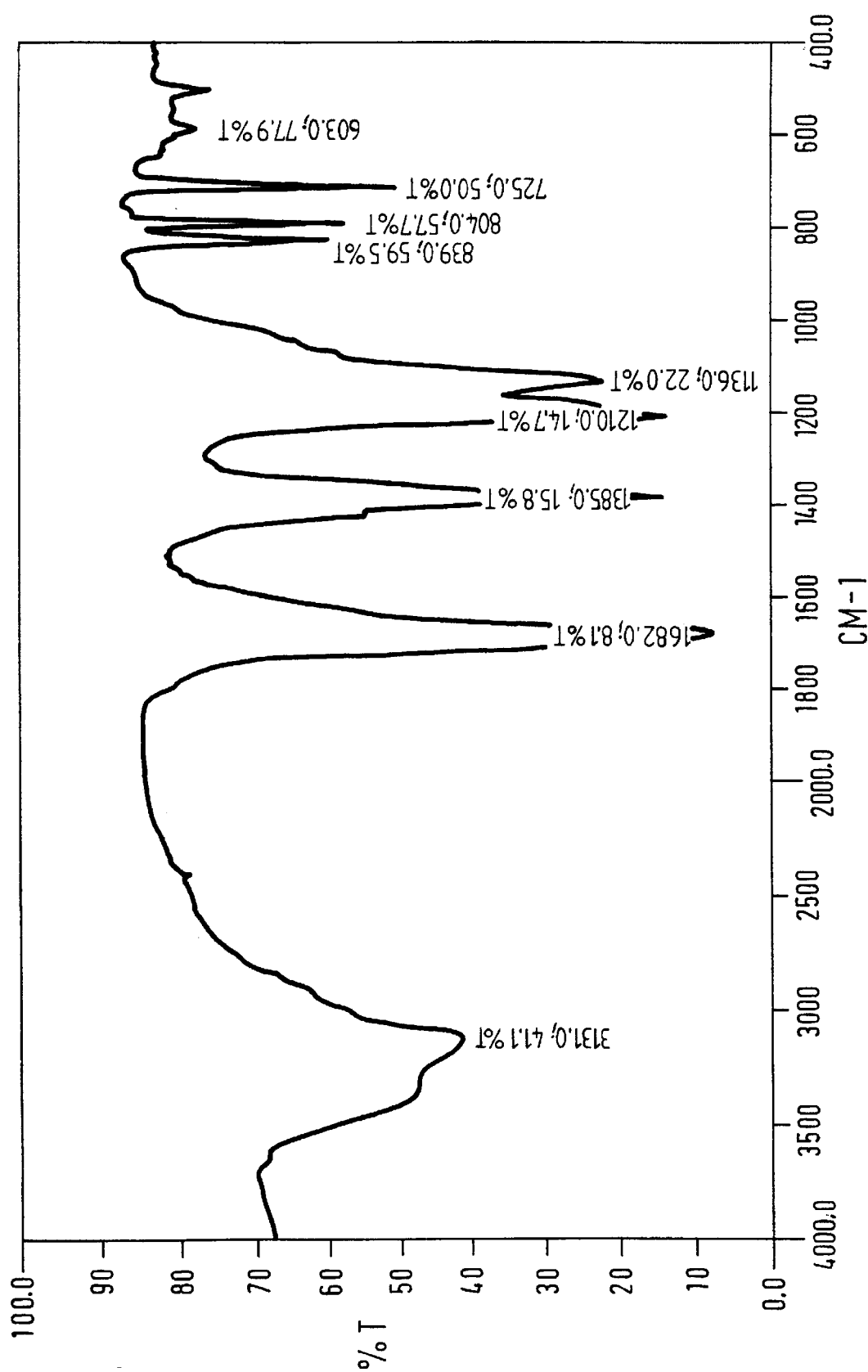
FIG. 5: Infrared spectrum in KBr pellets of the com-$(C_3O_2)_{10}$.

In general, the molecular spectra of the active substances according to the invention are relatively band-poor which coincides with the high symmetry of the corresponding structures. The infrared spectrum taken in KBr pellets (FIG. 5) demonstrates several characteristic absorption bands at 3500–3000 $cm^{-1}$, 1680–1620 $cm^{-1}$, 1400–1385 $cm^{-1}$, 1210 $cm^{-1}$, 1100 $cm^{-1}$, and between 830–600 $cm^{-1}$, whereby the strong band at 1660 $cm^{-1}$ is interpreted as a "ring breathing frequency" of the 4-pyrone ring. The absence of an IR absorption band at 1720 $cm^{-1}$ make a 2-pyrone structure improbable.

Figure 6:
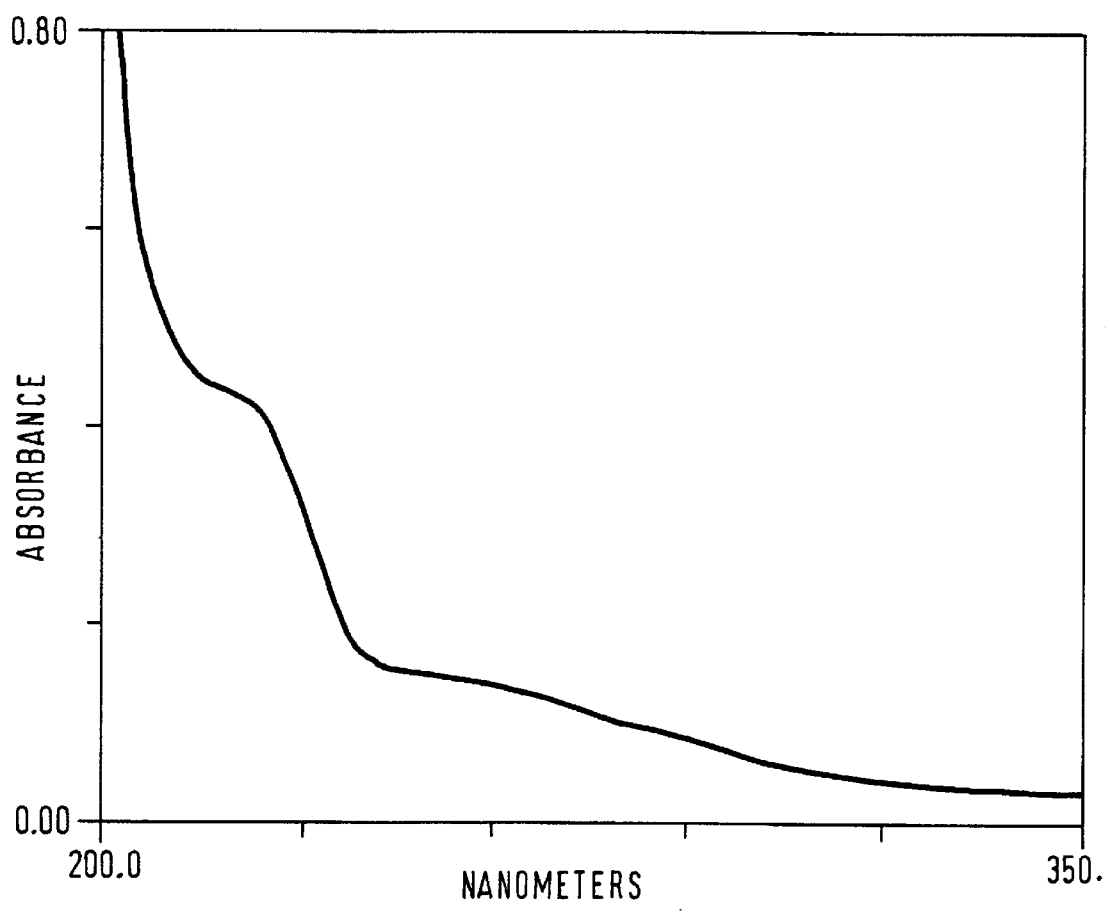
FIG. 6: UV-VIS absorption spectrum of the com-$(C_3O_2)_6$ in water.

The strongest absorption maximum of the UV-VIS spectra lies at ca. 190 nm with shoulders at ca. 220 nm and 265 nm (FIG. 6). As evident, instead of the expected strong absorption of the conjugated double bonds at ca. 320 nm, only a weak, non-specific sloping absorption from 240 to 400 nm is present. However, the inventor found for some adducts fluorescence emission in the range of 400–450 nm produced by excitation radiation at 310–340 nm. This can indicate that a stronger but symmetrically forbidden transition is present.

Analytical Reactions

The active substances of the formula com-$(C_3O_2)_n$ can be identified by a positive reaction with antimony pentachloride or with the Liebermann-Burchard reagent in thin layer chromatography. Silica gel-60 ready-to-use plates (Merck) and a elution mixture of 1-propanol:ethylacetate:and 20% acetic acid in the ratio 60:10:30 are used for the separation. As a spray reagent, a saturated antimony pentachloride solution in carbon tetrachloride or a mixture of 2 ml acetic anhydride and 2 ml concentrated sulfuric acid in 20 ml absolute ethanol is used. After spraying, the plates are heated ca. 10 minutes at 120° C. and examined in UV light at $\lambda$=365 nm. Fluorescing spots indicate the presence of the active substances according to the invention.

The active substances in the form of their amine adducts exhibit a positive ninhydrin reaction which can be used for their analytical detection or a spectrophotometric assay. Since this reaction is also exhibited by most amino acids and peptides, the analytic use is only suitable after a chromatographic separation. For a thin layer chromatography separation, silica gel-60 ready-to-use plates (Merck) and a mixture of 1-butanol:ethanol:water in the ratio 50:30:20 (v/v) is used as an eluent. As a spray reagent, 0.1% ninhydrin solution in ethanol which additionally contains 2% (v/v) glacial acetic acid and 0.5% (v/v) sym-collidine is used. Yellow spots in the Rf region 0.32 to 0.45 indicate the presence of some active substances according to the invention.

The hydroxy-pyran group of the active substances according to the invention exhibit a slightly positive phenol reaction with the Folin-Ciocalteu reagent and this can be used for an identification. Since the known Lowry method for protein determination is also based on this reaction, a chromatographic separation from proteins or phenolic substances must be conducted first.

Figure 7:
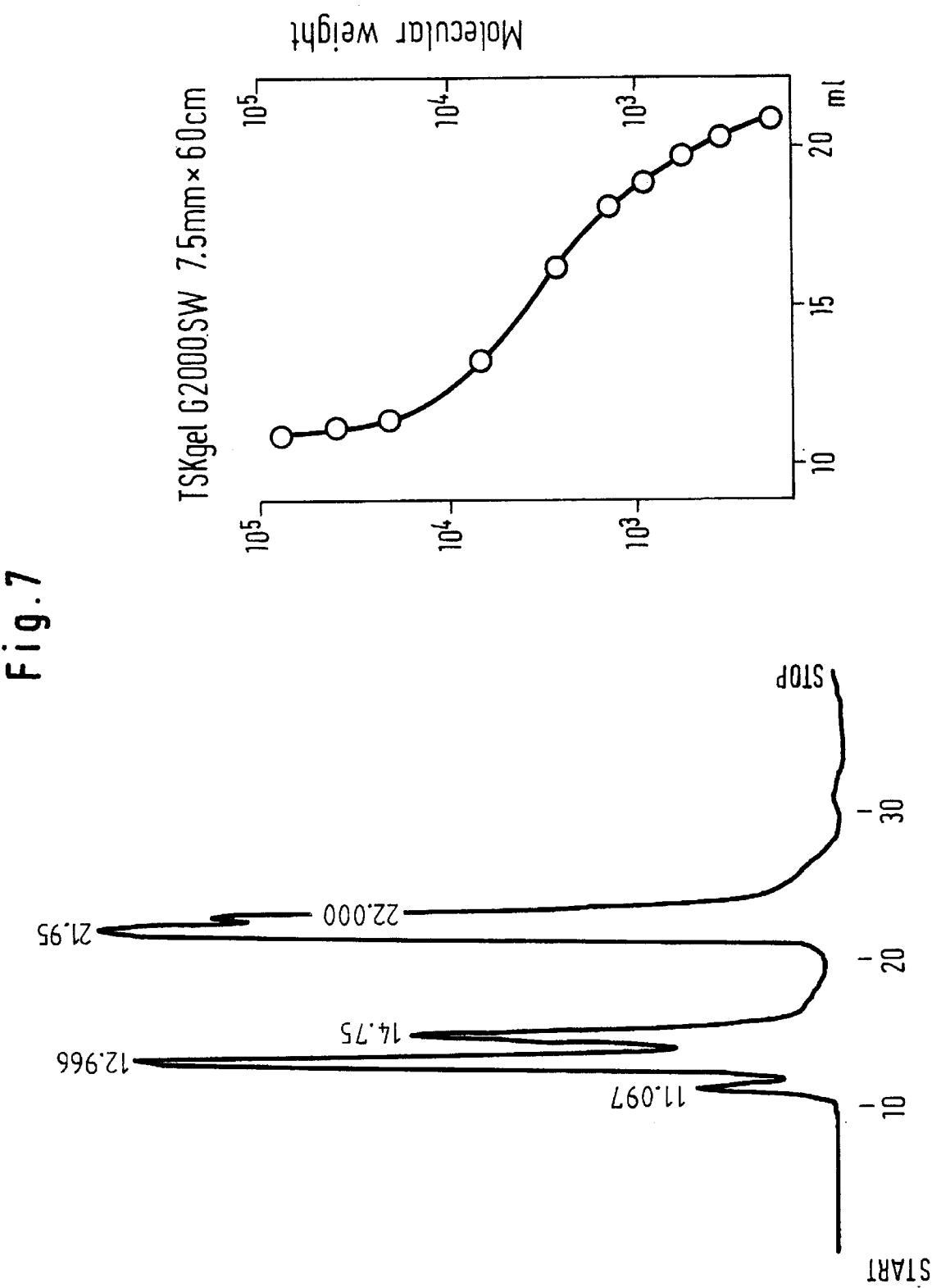
FIG. 7: HP-gel permeation chromatogram of an active substance mixture and the molecular weight standard curve of the column.

For an analytical separation according to molecular size of the substances according to the invention, the HP-GP method (high performance gel permeation chromatography) is used. The separation is carried out, preferably in a TSK G-2000 SW (Toso-Haas) column 600×7.5 mm with 50 mM borate buffer solution (pH=8.1) as an eluent. The molar masses of the active substance components in the mixture are established by means of the measured retention volumes (FIG. 7) with the aid of a calibration diagram (FIG. 7A). Polyethylene glycol standards with known molecular weight are used for the calibration curve.

For a chromatographic separation according to polarity of the components, the HPLC method with reversed phase is used, preferably with a Nucleosil 5 $C_{18}$ column (Macherey Nagel) as a solid phase and with a, preferably 10 to 90%, acetonitrile gradient in water as an eluent.

It is characteristic for the pyrylium salt derivatives according to the invention that they exhibit the known analytical reactions of the counter ions, for example the precipitation of the halogenides with silver ions or the sulfate ions with barium.

The active substances according to the invention exhibit a highly sensitive cross-reaction with the antibodies of cardiotonic steroid glycosides such as ouabain, digoxin and others. Since these organic compounds are not immunogenic as such, they are first chemically coupled to larger protein molecules such as BSA or avidin. By several fold administration of these conjugates to rabbits, the specific anti-ouabain or anti-digoxin antibodies are obtained. The cross-reaction of these antibodies with the active substances according to the invention is examined with the methods of enzyme-like immunoassay ELISA or radioimmunoassay (RIA). These techniques permit a highly sensitive assay of very small amounts of active substances (pg range). The assay in the human body fluids can be disturbed by the presence of cardiac glycosides which are only present in a specific medical treatment of heart diseases.

The active substances according to the invention of larger molar mass, M>2.0 kD, exhibit notable specific reactions with immunoglobulins. These immunospecific precipitation reactions with human or animal immunoglobulins are examined spectrophotometrically and by the Ouchterlouny method in agarose gel or by immunelectrophoresis according to Laurell. The notable difference between reactions with immunoglobulins from normal or from pathological sera enables the application of these reactions in the diagnosis of various immunopathologies.

O-alkyl and O-acyl Derivatives

Through the binding of inorganic or organic molecules of residues, designated by R, to the oxygen atoms of the basic frame, inorganic and/or organic derivatives or conjugates of the general formula:

$$com\text{-}(C_3O_2)_n\cdot R_m$$

are formed, wherein R=an inorganic or organic molecule and/or an organic residue, preferably methyl, ethyl, acetyl, benzyl, and $m \leq 2n$.

Production

According to the invention, carbon suboxide, which as far as it is concerned can be produced by known methods, can be used as a starting material for the synthetic production of the macrocyclic substances according to the invention.

According to the invention, $C_3O_2$ purified by fractional distillation is photochemically converted into the cyclooligomeric derivatives or by use of suitable auxiliary agents. The synthesis of carbon suboxide is carried out in a known manner by two-fold water elimination from smaller dicarboxylic acids such as malonic acid or its derivatives under influence of phosphorous pentoxide and/or by heating. However, in this method the formation of the undesired amorphous polymeric carbon suboxide develops. In contrast to this, the inventor has established that a thermal dehydration of the acid or its esters carried out in an aprotic solvent is much more suitable for the formation of the active substances according to the invention. According to the invention, the acid or the corresponding derivative is dissolved in an aprotic solvent, preferably dimethylformamide or acetic anhydride, by heating and stirring. The mixture is heated to 120–150° C., whereby the formation of $C_3O_2$ already appears after a few minutes. For the conversion of the carbon suboxide produced in this manner into the cyclooligomeric active substances according to the invention, a photochemical activation is applied and/or suitable auxiliary agents are added according to the invention. Those substances which act as a type of template for the formation of the macroring structure were found as effective auxiliary agents. Preferred are stable salt compounds of those ions whose radius corresponds to the internal cavity of the com-$(C_3O_2)_6$ macroring, internal diameter 2.9–3.1 Å. Preferred ions are rubidium (2.94 Å), potassium (2.66 Å), ammonia (2.86Å) and fluoride (2.72Å).

The inventor found that some enzymes, preferably those belonging to the class of the "Polyketide sythases" (PHSs) can be applied to synthesize the inventive cyclooligomerised and macroring closed derivatives of the carbon suboxide. Several carboxylic acid derivatives, preferably of malonic acid, preferably as malonyl-coenzyme A were applied. This malonyl coenzyme A can be readily prepared from acetyl-coenzyme A and $CO_2$ in the presence of biotin.

According to the invention, the inventive bioregulatory active substances can also be isolated from the side-products of some large-scale products starting from carbon monoxide. The inventor has surprisingly found that several known organic synthetic products whose industrial manufacture starts from carbon monoxide or from synthesis gas can contain low but detectable amounts of the active substances according to the invention. This can be explained with a low carbon suboxide content of CO and the synthesis gas. In order to increase the extremely low contents of active substances according to the invention in these large-scale products, fractional distillation methods are applied. 2 to 60 parts("parts" signifies "parts by weight" as long as nothing else is given), preferably 20 parts, water or aqueous buffer solution is added to 100 parts of the starting material, preferably industrial methanol produced from synthesis gas, and the methanol is at first distilled off from this mixture by application of a distillation column. The remaining water phase exhibits an increased content of the active substances according to the invention. By multiple repetition of the distillation with addition of fresh methanolic phases, a considerable concentration of the active substances according to the invention is obtained. The active substances according to the invention are isolated from this solution by application of fractional distillation or by absorption on solid phases, preferably charcoal or reversed phase silica, and desorption with the aid of solvent mixtures, preferably water-ethanol.

According to the invention, the inventive active substances are also isolated from plant extracts, plant cell cultures or from bacterial cultures. Numerous plant species were examined in which the active substances according to the invention are not present as such, but instead, as undefined conjugates of others, preferably toxic, plant components. Preferable crude material sources are those plant species which contain toxic components such as alkaloids or cardiotoxic glycosides. Furthermore, plant species with a relatively high content of saponins or tannins also offer a suitable starting material for the isolation of the active substances according to the invention. Roots, rootstocks, stems, leaves, bark or seeds or the corresponding plant cell cultures which are initiated by callus formation in a known manner are suitable as plant sources.

When the production of small molecular carbon suboxide derivatives, preferably com-$(C_3O_2)_n$, is desired, the following method is applied according to the invention: 10 parts extraction agent, preferably 30% of an alcohol-water mixture, is added to 1 part dried plant material de-fatted with hexane and macerated for 24 hours under light heating. The process is repeated several times, preferably 2–3 times, and the combined alcoholic extracts are concentrated. The concentrated tincture is boiled after addition of an acid, preferably acetic acid or hydrochloric acid, in an amount from 0.01 to 5%, preferably 1%, with respect to the tincture and maintained for a short time, preferably 10–30 minutes, at 80–100° C. The cooled solution is neutralized with a base, preferably $NH_4OH$, and treated with 1 to 20 parts, preferably 5–10 parts, charcoal per 100 parts liquid. The filtered charcoal is washed again with water and filtered. The charcoal dried under vacuum is treated with boiling extraction agent, preferably 1:1 ethanol-water, and the process is repeated 2 times. The solution of the active substances according to the invention obtained in this manner is stable and suitable for long-term storage. The combined solutions can also be concentrated and freeze-dried. The purification of the solid residue occurs by repeated recrystallization, preferably from alcohol-ether mixtures. The adducts isolated in this manner are stable for long-term storage.

When the production of high molecular cyclooligomeric carbon suboxide compounds is desired, the following method is applied according to the invention: 5–20, preferably 8, parts methanol are added to 1 part per weight dried plant material de-fatted with petroleum ether and macerated for 1 to 36, preferably 16, hours with light heating. The process is repeated several times, preferably twice, and the combined extracts are concentrated. The concentrated solution is incorporated into a water miscible, organic solvent, preferably acetone or ethanol, in a ratio of 1:20 to 1:2, preferably 1:8. The precipitate formed is separated by filtration or centrifugation and dissolved in minimal amounts of water or a buffer solution. The entire process is repeated 1–5 times, preferably 2 times. The crude product obtained in this manner is dissolved in a minimal amount of water alkalinized with a buffer of pH 9–10.5 and subjected to a dialysis against distilled water alkalinized with a buffer of pH 9–10.5 by using membranes, preferable with an exclusion limit of 3 kD. After a longer dialysis time, preferably after 3–4 days, with several replacements of the external membrane water amounts, the internal membrane solution is filtered, carefully concentrated and freeze-dried.

According to the invention, neutral absorbents or ionic solid phases, such as resins, gels or modified polysaccharides with ion exchange function are employed for the isolation of the inventive active substances of different molar mass. Due to the zwitterionic character of the active substances according to the invention, anionite—as well as cationite—or mixed bed exchange phases can be applied. At first, the extracts of vegetable or other origin are treated with the ion exchange phase. After the components are bound to the solid phase, the column is generously washed with an excess of neutral or weakly acidic eluent, preferably water or a buffer solution, until no customary contents (carbohydrates, amino acids) are detectable in the eluate. The desorption from the cationite phases occurs by using diluted mineral acids, preferably hydrochloric acid, or organic acids, preferably formic or acetic acid. The release of the active substances according to the invention bound to the anionic phases or mixed bed phases occurs by diluted alkali, preferably 0.1–0.3 molar ammonium or potassium hydroxide solution. The desorption from reversed phase silica occurs with solvents, preferably with methanol or aqueous acetonitrile.

According to the invention, the desorption from the neutral phases, such as silica gel, polyamides or various polysaccharides, occurs by using 0.2–5%, preferably 1.2%, sodium dodecylsulfate (SDS) solutions or from 1 to 12 molar, preferably 8 molar, urea solutions.

According to the invention, the separation and purification of the active substances of different molar mass according to the invention occurs with the aid of gel filtration or by membrane dialysis and ultrafiltration. For the separation of the active substances according to the invention according to their molecular sizes, gel chromatography is used with the aid of synthetic solid phases, preferably with Sephacryl 200, Sephadex LH-20 or TSK HW-60. As an eluent, weakly basic buffer solutions, preferably ammonium acetate or ammonium bicarbonate or a 0.01 to 0.3 molar, preferably 0.15 molar, NaCl or KCl solution, are used. With these separation methods, the compound with higher molecular weight is first eluted and the smaller compounds such as com-$(C_3O_2)_6$ or com-$(C_3O_2)_{10}$, later flow out of the column.

According to the invention, several conjugates which are formed from the active substances according to the invention with vegetable components can also be directly isolated. These mostly sticky, yellow-brown colored conjugates can be precipitated from the concentrated methanolic plant extracts by application of organic solvents, preferably acetone of diethyl ether. By several, preferably 3 to 5, repetitions of the precipitation, the conjugated obtained in this manner are relatively uniform. According to the invention, the following salting-out method can be used for the inventive cleavage of the conjugates. The conjugate is dissolved in water in which an inorganic salt, preferably ammonium sulfate, in an amount of 5 to 50% (w/w), preferably 15%, with respect to the final solution is additionally dissolved. An organic solvent, preferably n-butanol or 2-propanol, is incorporated into this solution and this is intensely shaken. The phases are separated and the process is repeated 2 to 5 times, preferably 3 times, whereby the pH value of the aqueous phase is adjusted with an acid to 1. After a further cleavage process according to the invention, the conjugate is dissolved in water, the pH value is adjusted to pH 10 with ammonia and the solution is stirred into a chlorinated solvent, preferably dichloromethane or chloroform, in a ratio of 1:0.5 to 1:6, preferably 1:2. The very stable, foamy emulsion formed by powerful shaking is separated and the organic solvent is removed therefrom under reduced pressure.

The active substances according to the invention can also be isolated from bacterial starting materials. For this, bacterial cultures of various types, preferably *BCG* (*Bacillus Cualmette-Guérin*), *Corynebacterium parvum* or *Escherichia coli* can be used according to the invention. First, a physical treatment, preferably ultrasound treatment, and a hydrolysis by application of diluted mineral acids, preferably hydrochloric acid, is carried out. The filtered hydrolysate is optionally neutralized and applied to a solid phase, preferably normal or reversed phase silica gel. The solid phase is treated with various neutral elution agents until no amino acids, carbohydrates and other simple hydrolysis products are detectable in the eluate. The desorption of the active substances according to the invention occurs with the aid of diluted alkali, preferably with 0.1 to 0.2 molar ammonium hydroxide or with methanol or aqueous ethanol or acetonitrile for the reversed phase.

Animal tissue and tissue fluids can contain small amounts of the active substances according to the invention as undefined conjugates. According to the invention, an organic extraction of the tissue of the carefully freeze-dried organic fluids, preferably urine, is first carried out. The active substances according to the invention are isolated and purified from the concentrated organic extract by using selective affinity chromatography methods. For this purpose, a known cardiac glycoside, preferably ouabain or hellebrin, is covalently bound to a solid phase, preferably Sepharose. This affinity phase retains the active substances according to the invention from the concentrated crude material solution. After multiple washings of the column with weakly acidic or neutral buffer solutions, the compounds according to the invention are released with the aid of alkaline buffer solutions.

Bioregulatory Applications

The inventor has found that the active substances according to the invention effectively control the activity of the $Na^+,K^+$-ATPase enzyme which is also known as the sodium pump. This widely distributed enzyme regulates the extra- and intracellular concentration of the most important alkali metal ions by so-called active membrane transport. The energy necessary for this is delivered by the hydrolysis of ATP, which is directly coupled with the activity of this enzyme. The active substances according to the invention are capable to control the complex activity of this enzyme. The direction and intensity of this control is dependent on the concentration and on the molar mass of the active substances according to the invention. The nature and concentration of the alkali metal ions present and the other inorganic ions can substantially influence this controlling effect. With the addition of the active substances according to the invention to an erythrocyte suspension, an increase of the extracellular Na concentration, i.e. an activation of the sodium pump, was observed. In contrast, an inhibition of the $Na^+,K^+$-ATPase enzyme was established in vitro and with particular concentrations of the active substances of smaller molar mass according to the invention.

A reduction of the toxic side-effects of ouabain or of other cardiac glycosides was also observed when the active substances according to the invention were applied together with these glycosides. With the addition of the active substances according to the invention in a molar ratio between 0.02 to 2/1 mol glycoside, preferably 1:1, the $LD_{50}$ value of hellebrin was considerably higher which signifies a decrease of the acute toxicity. Furthermore, as was experimentally established, the active substances according to the invention are capable to control the activity of several other essential enzymes, for example collegenases, hyaluronidases, phosphokinases and other enzymes. According to all indications, the active substances according to the invention are useable as endogenous ligands of the $Na^+,K^+$-ATPase enzyme.

Immunoregulation

The inventor has found several immunoregulatory actions for the substances according to the invention. These mechanisms can also partially be explained with the above described control of the $Na^+,K^+$-ATPase because this enzyme substantially participates in a large number of immunological processes.

Furthermore, a new immunoregulatory effect of the active substances according to the invention is achieved in that these have a specific affinity for the Fc receptors. These receptors are anchored on various immunocytes and their occupation or non-occupation plays a fundamental role in the control of activity of these cells. In clinical tests, the active substances according to the invention led to a considerable suppression of the activity of pathologically activated killer cells (K cells) and other lymphocytes in the antibody dependent cellular cytotoxicity (ADCC). In contrast, the activity of natural killer cells (NK cells) in the spontaneous cellular cytotoxicity (SCMC) was differently influenced by the active substances according to the invention: with rheumatic patients, the pathological overstimulated spontaneous cytotoxicity is clearly suppressed. With health test persons, the spontaneous cytotoxicity was only insignificantly influenced. Therewith, the clinical data prove that, by a suppression of pathological autoaggresive processes, the active substances according to the invention are suitable for a causal rheumatic therapy or for prevention of tissue or organ graft rejection. It is important to note that all of these effects were obtained with uncommonly small amounts of active substance in the range of $\mu g/kg$. On the other hand, the toxicity of the compounds according to the invention is extremely low. Therewith, the most important pharmacotoxicological prerequisites are fulfilled for human therapeutical applications according to the invention. The rheumatic therapeutic use of the active substances according to the invention offers an additional clear advantage. The small cyclooligomer com-$(C_3O_2)_n$ preferably with n=6 and its adducts exhibit an uncommonly strong analgesic and spasmolytic effect. The analgesic and spasmolytic effect appearing immediately after a local administration offers an important advantage for rheumatic therapy applications. The quickly appearing relief from pain and spasmolysis are maintained long-term by the re-establishment of normal immunoregulation. The active substances with larger molecular mass according to the invention are capable to exert a notable non-specific effect which mimics immunostimulation. This was unequivocally confirmed in animal experiments with bacterial infections. The animals treated with active substances had considerably longer survival rates with lethal Pseudomonas aeruginosa doses than the animals in the control group.

The bioregulatory active substances according to the invention can be administered either separately as pure substances or as substance mixtures or in the form of pharmaceutical compositions, whereby the latter named can comprise one and/or several pharmaceutically safe adjuvants and/or carriers aside from the substances according to the invention. As these substances, 0.9% sodium chloride solution, 1 to 5% glucose or fructose solution, carboxymethylcellulose, potato starch, lactose, lanolin, mannite, magnesium stearate, 1,2 propyleneglycol, glycerin, cetylstearyl alcohol, nipagin, sodium lauryl sulfate and talcum may be named. Optionally, still further therapeutically active substances or adjuvants can be added to the pharmaceutical compositions produced in this manner. These galenic formulations include all those formulations which are suitable for parenteral, intramuscular, intravenous, subcutaneous, peri- or intra-articular injections, a peroral application such as by means of tablets, capsules or drops, or an external application such as by means of ointments, creams, gels or suppositories.

The present invention is illustrated further in the following examples.

EXAMPLE 1

Synthetic production from carbon suboxide

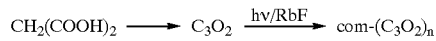

In a glass reactor which is equipped with a reflux water cooler, 15 parts malonic acid are dissolved in 80 parts acetic anhydride by heating with an oil bath (80° C.) and stirring. In an extension of the reflux cooler, two further dry ice cooling traps are connected in order to collect the arising volatile compounds. After the entire amount of acid is dissolved, 0.2 parts rubidium fluoride are added and a photochemical irradiation is carried out with a 250 W sun lamp. An increase of the oil bath temperature results up to 130–150° C. and the reaction mixture becomes increasingly darker brown. The carbon suboxide which is volatile under strong vacuum and its derivatives are condensed in the traps cooled with dry ice and acetone. The condensate is purified by fractional vacuum distillation. The active substances obtained in this manner are purified and analyzed by known chromatographic methods.

EXAMPLE 2

Isolation from Industrial Methanol 250 parts 0.1 molar ammonium acetate buffer solution of pH 9 are added to 1000 parts methanol produced from synthesis gas and the methanol is first distilled off from this mixture by application of a distillation column. 1000 parts methanol are again added to the remaining water phase and the distillation of the methanol is repeated 3–4 times. The water phase remaining in the end is carefully concentrated and treated with charcoal. 50 parts of the charcoal separated by filtration and dried in air are treated with 400 parts water containing 80% (v/v) ethanol at 80–90° C. and warm filtered after 30 min maceration. The extraction is repeated 2 times. The combined ethanolic extracts are carefully concentrated and freeze-dried.

EXAMPLE 3
Isolation from Helleborus Species

Parts of dried and coarsely minced root and rootstock of *Helleborus purpurascens* (family Ranunculaceae) are de-fatted with 120 parts hexane and subsequently pre-extracted with 80 parts methylene chloride. After removal of the extraction agent, the dried residue is macerated with 200 parts water containing 30% (v/v) ethanol during 24 hours at room temperature. The extraction is repeated twice and subsequently the combined extracts are filtered and concentrated under vacuum. 250 parts of the extract obtained in this manner are added to 3 parts concentrated hydrochloric acid and heated for 20 minutes at 95° C. After the neutralization, the solution is treated with a little charcoal and filtered. The filtrate concentrated under vacuum is poured into the 8-fold volume acetone, the centrifuged precipitate is dissolved in a minimal amount of water and repeatedly precipitated 2–3 times with acetone. The precipitate is dissolved in minimal 0.1 molar sodium chloride solution and the solution is led over a gel column filled with TSK HW-60. The elution occurs at a flow rate of 5 cm/h with 0.125 molar ammonia solution in water, which also contains 10% (v/v) 2-propanol. The detection occurs by measurement of the optical density at 230 nm.

EXAMPLE 4
Isolation of the Active Substances from Seeds of *Vitis Vinifera*

25 parts dried and ground seeds of *Vitis vinifera* are added to 150 parts 0.5 molar borate buffer with pH=9.6 and heated and macerated for 30 minutes at 90° C. The filtered solution is concentrated and poured into the 8-fold volume of cooled ethanol under stirring. The precipitate resulting thereby is centrifuged and dissolved in a minimal amount of water and precipitated twice each with the 6-fold amount of cooled ethanol. The precipitate dissolved in a minimal amount of ammonium acetate buffer solution with slightly alkaline pH is subjected to a separation by ultrafiltration, where membranes with molecular exclusion limits of 30, 10, 3 and 1 kD are used. The pH of the fractions separated in this manner is readjusted to a weakly acidic pH value and lyophilized.

EXAMPLE 5
Active Substance Isolation from *Phytolacca Americana*

100 parts dried roots from *Phytolacca americana* are minced to a particle size of 0.5–1.2 mm and de-fatted with 600 parts hexane by a treatment lasting 24 hours. At first, the hexane is pressed off and the plant material is air dried until the hexane odor is no longer perceptible. The dried plant material is macerated with 800 parts water containing 5% (v/v) acetic acid for 4 hours at room temperature and the process is repeated twice. The combined extracts are filtered and concentrated under vacuum. 15 to 50 parts ammonium sulfate are added stepwise to 100 parts of the aqueous solution and dissolved. The proteins precipitated by salting-out are removed by centrifugation and filtration. 50 parts 1-butanol are given to 50 parts supernatant and this is strongly shaken. After some time, the organic phase is separated and the extraction with butanol is repeated twice. The combined butanolic solutions are back extracted with water containing 0.1% ammonia. The aqueous phase is concentrated under vacuum and purified by gel filtration.

EXAMPLE 6
Production from *Escherichia Coli*

2000 volume parts autoclaved culture medium which contains 20 parts tryptone, 10 parts yeast extract, 20 parts NaCl and 30 parts agar and is supplemented with the suitable nutritional additives is inoculated with *Escherichia coli* strain K-12 in a dilution of 1:100. The culture is maintained at 37° C. until a saturation density of $2 \times 10^9$ cells/ml is attained. The reaction mixture is exposed to an ultrasound treatment and heated with 1.0 N acetic acid for 20 min at 90° C., filtered after cooling and concentrated under vacuum. 150 parts of the concentrated solution are absorbed on reverse-phase silica (RP18)for column chromatography (Merck) and the solid phase is first washed with water containing 2% (v/v) acetic acid, thereafter with 1000 parts buffer mixture comprising n-propanol:ethyl acetate:20 mM borax/borate buffer in the ratio 600:100:300% (v/v) and washed at the end with water. The solid phase is washed so long with these neutral elution agents until no amino acids, carbohydrates and other simple hydrolysis products are detectable in the eluate. The desorption of the active substances according to the invention occurs with acetonitrile, whose excess is removed by concentration under vacuum. The solution of the active substances according to the invention obtained in this manner is concentrated.

EXAMPLE 7
Isolation from Animal Fluids 10,000 parts porcine urine are freeze dried and the solid residue is extracted three times with 600 parts methanol. The methanolic extracts are concentrated to 20 parts. 100 parts cyanogen bromide-activated Sepharose 4B is treated for 90 minutes with a solution of suitably activated hellebrin until 80% of the glycoside used is covalently bound to the solid phase. 10 parts concentrated methanolic solution are applied to the affinity chromatography column prepared in this manner and eluted for such a time until no more chemical compounds are detectable in the eluate. The active substance according to the invention is eluted from the column by gradient elution with 0.5 to 0.2 molar formic acid and freeze-dried. The purification of the active substances occurs on a column filled with Sephadex LH-20 (Pharmacia). The active substances are first absorbed onto the column and eluted with a gradient of 20 to 60 (v/v) % acetone in water.

EXAMPLE 8
Immunomodulatory Application

The spontaneous cell mediated cytotoxicity (SCMC) of NK cells was measured by the assay of $^{51}$Cr isotope released from the $K_{562}$ target cells in a 100/1 to 10/1 effector/target ratio. In 8 of 10 healthy subjects, the active substance according to the invention elevated the lytic activity with an average of 15%. The pathological SCMC activity of 16 rheumatic patients, patologically increased to an average of 141%, was clearly normalized by the administration of the active substances according to the invention. The effector cells in the antibody dependent cellular cytotoxicity (ADCC) are influenced in a much more uniform manner by the active substances according to the invention. As evident from the following Diagram 1, the ADCC activity is diminished in healthy as well as in rheumatic patients.

Diagram 1
Cytotoxicity of healthy and rheumatic patients with and without active substance treatment

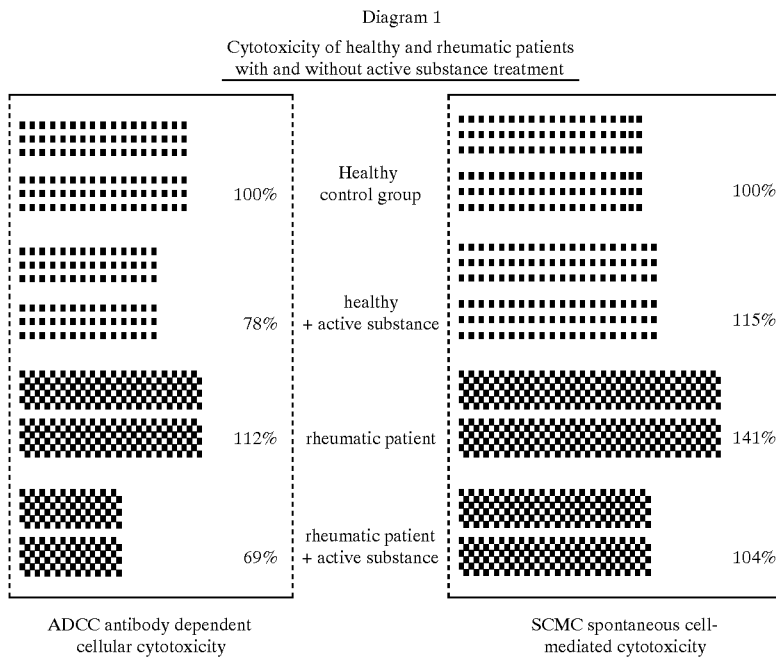

ADCC antibody dependent cellular cytotoxicity

SCMC spontaneous cell-mediated cytotoxicity

This normalization of the activity can be explained by the specific affinity of the active substances on the Fc receptor.

EXAMPLE 9

Immunosuppressive Application for Organ Transplantation

The immunosuppressive action of the substances according to the invention led to a clear reduction of the graft-rejection reactions in organ transplantations. This was experimentally proven with the aid of a series of experimental heart transplantations in mice.

The method for allograft heart transplantation of Corry, R., Winn, H. and Ressel, P., Transplantation 16, 343 (1973) was applied to pathogen-free, 5–6 week old mice of the line Sprague Dawley DBA/2 as a donor and C57BL/6 as a recipient.

After intravenous heparinization of the animals used as a doner, their hearts were removed and maintained in ice cold Ringer's lactate solution until preparation of the C57BL/6 recipient animals. The anastomosis between aorta and lung arteries of the doner with the abdominal aorta and vena cava of the recipient was produced by microsurgical techniques.

After the re-establishment of blood flow, the frequency and intensity of the heart beat was observed and rated from 0 to +4. The rejection was established after cessation of the pulse and visualized by laparotomy. The mice in the test group had obtained the following amounts of active substances by subcutaneous administration:

2.0 mg/kg three days before the transplantation 3.0 mg/kg on the day of the operation 2.5 mg/kg on the third post-operative day 1.5 mg/kg every third day thereafter The animals in the control group were only treated with citrate buffer as a placebo.

In these transplantation experiments, the following results were obtained:

| Animal Nr. | Treatment with: | survival time (days) |
| --- | --- | --- |
| 1 | active substance | 24 |
| 2 | active substance | 31 |
| 3 | active substance | 18 |
| 4 | active substance | 21 |
| 5 | active substance | 42 |
| 6 | active substance | 18 |
| 7 | active substance | 6 |
| 8 | active substance | 33 |
| 9 | active substance | 12 |
| 10 | active substance | 22 |
| 11 | placebo | 8 |
| 12 | placebo | 6 |
| 13 | placebo | 10 |
| 14 | placebo | 9 |

The average survival rate of the animals treated with placebo was 8.2 days. With an average value of 22.7 days, the animals treated with active substance exhibited a clear, almost hree-fold as long survival time as the placebo animals. This effect is explained by the specific suppression of the T lymphocytes causing the rejection reaction.

EXAMPLE 10

Stimulation of Macrophages

The spleen lymphocytes from 10 normal mice were suspended in $RPMI_{1640}$ medium buffered with HEPES and supplemented with 10% fetal calf serum. The suspension was maintained at 37° C. for 1 hour in order to permit the adherence of the macrophages. In the test group, the mice were treated intraperitoneal with 5 mg/kg active substance and sacrificed 24 hours thereafter. The animals of the control group did not receive any active substance. The lymphocytes from both groups were cultivated in tubes containing $5 \times 10^5$ adhering macrophages.

Stimulation index of the macrophages

|  | LPS | PHA |
| --- | --- | --- |
| control group | 288% | 165% |
| active substance group | 402% | 1,346% |

As evident, the stimulation indices (SI) attained by LPS (Lipopolysaccharide) and PHA (phytohemagglutinin) in the animals treated with active substance are significantly larger.

EXAMPLE 11
Application for Apparent Immunostimulation

A non-specific apparent immunostimulation was examined by the determination of the survival rates of animals which were infected with a lethal dose of *Pseudomonas aeruginosa*.

In three test groups of 30–100 mice respectively, each animal received the lethal dose of *Pseudomonas aeruginosa*.

I. On the 7th, 14th and 28th day before the lethal Pseudomonas infection, 2 µg active substance was administered in the first group; on the 21st day, 0.25 ml physiological NaCl solution, II. In the second group, the same active substance doses as in the group I, however, on the 21st day, 0.06 mg cyclophosphamide, III. The control group was not given any active substances.

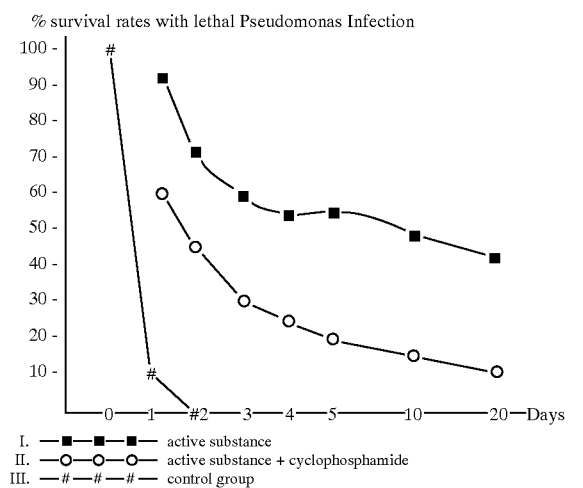

% survival rates with lethal Pseudomonas Infection

I. —■—■—■— active substance
II. —O—O—O— active substance + cyclophosphamide
III. —#—#—#— control group The active substances according to the invention caused a clear increase of the survival rates. Although the survival rates were lowered by the known immunosuppressive effect of cyclophosphamide, they clearly remain over the values of the control group. The interaction indicates a non-specific apparent immunostimulation of the active substances according to the invention, wherein a novel immune mechanism not described up to now would also be imaginable. It was recently proven that immediately after the administration of the lethal Pseudomonas dose, a explosion-like release of cytokines takes place. The cytokine shock condition triggered thereby is assumed as the immediate cause of sudden death. The immunosuppressive effect according to the invention can prevent this cytokine shock and leads to astonishingly greater survival rate without having exercised a true immunostimulation.

EXAMPLE 12
Assay of the Active Substances with the Aid of Competitive ELISA Methods For the assay, the cross-reaction of the active substances according to the invention with anti-ouabain (a-OU) antiserum is used. The ouabain-avidin conjugate (OU-con) was synthesized from pro analysi ouabain (Sigma) and avidin (Fluka) according to the methods of Harris et al., Hypertension 17, 930 (1991). The improvements of V. DiBartolo et al., Life Sciences, 57, 1417 (1995) were applied in the production of the corresponding anti-ouabain serum.

The ELISA microtiter plates were first incubated each with 0.1 µg/50 µl OU-con conjugate solution overnight at 4° C. Non-bound conjugates were washed out with phosphate buffer (PBS, pH=7.4) and the non-occupied binding sites were blocked with 1% gelatin solution.

50 µl from the sample solution with the unknown content of active substance was mixed together with constant amounts of anti-ouabain serum (0.5 µg/50 µl) in polypropylene tubes and held at room temperature for 2 hours. Thereafter, 50 µl from each active substance antiserum sample was applied to the plates and incubated for a further 3 hours. After washing out the non-bound antiserum with PBS, the plates were treated with a 1:500 solution of protein A alkaline phosphatase (Sigma) for 2 hours at room temperature. After removal of the non-bound enzyme, the plates were each treated with 50 µl p-nitrophenyl phosphate solution (1 mg/ml), and after 30 min incubation time, the absorption values (A) at 405 nm were automatically read.

For the construction of a calibration curve, known amounts of active substance in the range 5 ng/ml to 0.1 mg/ml were mixed with constant amounts of antiserum, treated according to the above named methods and the measured absorption values were depicted as a function of the corresponding concentrations.

What is claimed is:

1. A macrocyclic compound consisting of n carbon suboxide ($C_3O_2$) units which form n linearly condensed 4-pyrone or 2-pyrone rings which are joined in a macrocycle, wherein n is 4, 6, 8 or 10.

2. The macrocyclic compound of claim 1, wherein n is 6 and said macrocyclic compound has six head-to-tail condensed 4-pyrone rings depicted as follows:

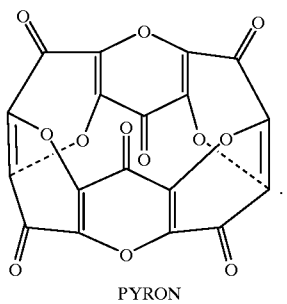

PYRON

3. An oligomer of the macrocyclic compound of claim 1, wherein said oligomer has an oligomerization degree s of 2, 3, 4, 5, 6, 10 or 12.

4. The oligomer of claim 3, wherein s is 12 and n is 6, and the molar mass of said oligomer is about 4,898 Da.

5. An adduct formed between the macrocyclic compound of claim 1, and an inorganic compound selected from the group consisting of hydrogen, water, ammonia and an alkali salt.

6. An adduct having a hydroxy-pyran structure formed between the macrocyclic compound of claim 1, and m hydrogen atoms, wherein $m \leq n$.

7. An adduct having a hydroxy-pyran structure formed between the macrocyclic compound of claim 1, and m $H_2O$ molecules, wherein m≦n.

8. An adduct between the macrocyclic compound of claim 1 and m molecules of ammonia, wherein m≦n.

9. An adduct between the macrocyclic compound of claim 1 and m equivalents of an alkali salt, wherein m≦n.

10. An adduct formed between the oligomer of claim 3, and an inorganic compound selected from the group consisting of hydrogen, water, ammonia and an alkali salt.

11. A pharmaceutical composition comprising:
(A) a member selected from the group consisting of:
  a macrocyclic compound consisting of n carbon suboxide ($C_3O_2$) units which form n linearly condensed 4-pyrone or 2-pyrone rings which are joined in a macrocycle, wherein n is 4, 6, 8 or 10,
  an oligomer of a macrocyclic compound consisting of n carbon suboxide ($C_3O_2$) units which form n linearly condensed 4-pyrone or 2-pyrone rings which are joined in a macrocycle, wherein n is 4, 6, 8 or 10, wherein said oligomer has an oligomerization degree s of 2, 3, 4, 5, 6, 10 or 12,
  an adduct formed between a macrocyclic compound consisting of n carbon suboxide ($C_3O_2$) units which form n linearly condensed 4-pyrone or 2-pyrone rings which are joined in a macrocycle, wherein n is 4, 6, 8 or 10, and an inorganic compound selected from the group consisting of hydrogen, water, ammonia and an alkali salt, and
  an adduct formed between an oligomer of a macrocyclic compound consisting of n carbon suboxide ($C_3O_2$) units which form n linearly condensed 4-pyrone or 2-pyrone rings which are joined in a macrocycle, wherein n is 4, 6, 8 or 10, wherein said oligomer has an oligomerization degree s of 2, 3, 4, 5, 6, 10 or 12, and an inorganic compound selected from the group consisting of hydrogen, water, ammonia and an alkali salt; and
(B) a pharmaceutically acceptable carrier.

12. A method for inhibiting the transport of alkali metal ions through the cell membrane comprising contacting cells with an effective amount of a macrocyclic compound of claim 1.

13. A method for promoting transport of membrane impermeable ions through the cell membrane comprising contacting cells with an effective amount of an oligomer of claim 3.

14. A method for diminishing acute or chronic toxicity of a therapeutic substance selected from the group of a natural alkaloid, cardiac glycoside and synthetic medicament, comprising administering said substance in combination with the pharmaceutical composition of claim 11.

15. A method for improving the bioavailability of a pharmaceutically active substance selected from the group of a steroid, peptide and synthetic derivatives thereof comprising administering to a subject said substance in combination with the pharmaceutical composition of claim 11.

16. A method for treatment of inflammation associated with chronic diseases or with acute injuries comprising administering to a subject in need of such treatment, the pharmaceutical composition of claim 11.

17. A method for treatment of pain associated with chronic diseases or with acute injuries comprising administering to a subject in need of such treatment, the pharmaceutical composition of claim 11.

18. A method for treatment of pain associated with muscular or blood vessel spasms comprising administering to a subject in need of such treatment, the pharmaceutical composition of claim 11.

19. A method for treatment of rheumatic diseases comprising administering to a subject in need of such treatment, the pharmaceutical composition of claim 11.

20. A method for treatment of autoimmune diseases comprising administering to a subject in need of such treatment, the pharmaceutical composition of claim 11.

21. A method for treatment of rheumatoid arthritis, multiple sclerosis, lupus erythematosus, or myasthenia gravis comprising administering to a subject in need of such treatment, the pharmaceutical composition of claim 11.

22. A method for suppression of graft-rejection reaction in organ or tissue transplantation comprising administering to a subject in need of such suppression, the pharmaceutical composition of claim 11.

23. A method for treatment of a disease caused by acutely or chronically weakened immune defenses or cytokine-mediated shock phenomenon comprising administering to a subject in need of such treatment, the pharmaceutical composition of claim 11.

24. A method for treatment of a cardiovascular pathology caused by defective bioregulation of the $Na^+$, $K^+$-ATPase system comprising administering to a subject in need of such treatment, the pharmaceutical composition of claim 11.

* * * * *